US012623118B2

(12) United States Patent
Seppänen et al.

(10) Patent No.: US 12,623,118 B2
(45) Date of Patent: May 12, 2026

(54) METHOD AND APPARATUS FOR ASSESSING ACCLIMATIZATION TO ENVIRONMENTAL CONDITIONS AND TO ASSESS FITNESS LEVEL TAKING INTO ACCOUNT THE ENVIRONMENTAL CONDITIONS AND THE LEVEL OF ACCLIMATIZATION

(71) Applicant: Garmin Jyväskylä Oy, Jyväskylä (FI)

(72) Inventors: Mikko Seppänen, Jyväskylä (FI);
Kaisa Hämäläinen, Jyväskylä (FI);
Joonas Korhonen, Jyväskylä (FI);
Sami Saalasti, Jyväskylä (FI); Aki Pulkkinen, Jyväskylä (FI); Tero Myllymäki, Jyväskylä (FI); Wille Hujanen, Jyväskylä (FI); Joonas Koskinen, Jyväskylä (FI)

(73) Assignee: Garmin Jyvaskyla Oy (FI)

( * ) Notice: Subject to any disclaimer, the term of this patent is extended or adjusted under 35 U.S.C. 154(b) by 0 days.

(21) Appl. No.: 18/646,083

(22) Filed: Apr. 25, 2024

(65) Prior Publication Data

US 2024/0307739 A1      Sep. 19, 2024

Related U.S. Application Data

(63) Continuation of application No. 16/794,466, filed on Feb. 19, 2020, now Pat. No. 11,998,802.

(30) Foreign Application Priority Data

Feb. 19, 2019      (FI) ..................................... 20195128

(51) Int. Cl.
G16H 20/30          (2018.01)
A61B 5/00          (2006.01)
(Continued)

(52) U.S. Cl.
CPC ...... A63B 24/0062 (2013.01); A61B 5/02438 (2013.01); A61B 5/0255 (2013.01);
(Continued)

(58) Field of Classification Search
CPC ......... A61B 5/01; A61B 5/024; A61B 5/0205; A61B 5/0255; A61B 5/02438;
(Continued)

(56) References Cited

U.S. PATENT DOCUMENTS 3,280,636 A       10/1966   Tomberg
4,724,845 A  *    2/1988    Callahan .............. A61B 5/0833
                                                                        600/531
(Continued)

FOREIGN PATENT DOCUMENTS

CN          1968293 A  *   5/2007
EP          3175782 A1     6/2017
(Continued)

OTHER PUBLICATIONS

Finnish Office Action and Search Report issued on Aug. 23, 2019 in corresponding Finnish Application No. 20195128; 7 pages.
(Continued)

*Primary Examiner* — Steven J Hylinski
(74) *Attorney, Agent, or Firm* — Samuel M. Korte; Max M. Ali; Kathleen D. Fitterling

(57)          ABSTRACT

A system of estimating acclimatization to environmental conditions and providing a corrected fitness level estimates based on the acclimatization level. The environmental conditions are particularly related to heat and altitude. At first previous training history is provided including a plurality of day records, where each day record includes a date stamp and information regarding altitude and optionally tempera-
(Continued)

ture and humidity and training history including timestamp and training load data from executed exercises in stored records.

7 Claims, 6 Drawing Sheets

(51) Int. Cl.
 *A61B 5/024* (2006.01)
 *A61B 5/0255* (2006.01)
 *A63B 24/00* (2006.01)
(52) U.S. Cl.
 CPC .......... *A61B 5/7225* (2013.01); *A61B 5/7475* (2013.01); *G16H 20/30* (2018.01); *A61B 2560/0252* (2013.01); *A61B 2562/0219* (2013.01); *A61B 2562/029* (2013.01); *A63B 2024/0065* (2013.01); *A63B 2220/12* (2013.01)
(58) Field of Classification Search
 CPC ........ A61B 2560/0252; A63B 24/0062; A63B 2024/0068; G16H 20/30; G16H 50/30
 See application file for complete search history.

(56) References Cited

U.S. PATENT DOCUMENTS

| | | | |
|---|---|---|---|
| 6,111,501 A | 8/2000 | Honeyager et al. | |
| 6,556,852 B1 | 4/2003 | Schulze et al. | |
| 7,396,157 B2 | 7/2008 | Liao | |
| 7,942,825 B2 | 5/2011 | Ranganathan et al. | |
| 8,157,731 B2 | 4/2012 | Teller et al. | |
| 8,275,635 B2 | 9/2012 | Stivoric et al. | |
| 8,325,030 B2 * | 12/2012 | Townsend ............... | G01W 1/17 340/521 |
| 8,784,115 B1 | 7/2014 | Chuang | |
| 8,830,068 B2 | 9/2014 | Campbell et al. | |
| 8,922,365 B2 | 12/2014 | Liu | |
| 8,961,415 B2 | 2/2015 | Leboeuf et al. | |
| 9,597,038 B2 | 3/2017 | Schwiening et al. | |
| 10,123,730 B2 | 11/2018 | Saalasti et al. | |
| 10,456,077 B1 | 10/2019 | Chuang | |
| 10,499,849 B1 | 12/2019 | Chuang | |
| 10,856,794 B2 | 12/2020 | Saalasti et al. | |
| 11,246,493 B2 | 2/2022 | Kim et al. | |
| 11,317,862 B2 | 5/2022 | Myllymäki et al. | |
| 11,318,351 B2 | 5/2022 | Pulkkinen et al. | |

| | | | |
|---|---|---|---|
| 2002/0009119 A1 | 1/2002 | Matthew et al. | |
| 2002/0039952 A1 | 4/2002 | Clem | |
| 2003/0013072 A1 | 1/2003 | Thomas | |
| 2005/0004488 A1 * | 1/2005 | Hoppe ................. | A61B 5/0833 600/529 |
| 2006/0004265 A1 | 1/2006 | Pulkkinen et al. | |
| 2006/0032315 A1 | 2/2006 | Saalastic et al. | |
| 2006/0063980 A1 | 3/2006 | Hwang et al. | |
| 2007/0100666 A1 * | 5/2007 | Stivoric ................... | G05B 1/01 374/E1.002 |
| 2007/0232455 A1 | 10/2007 | Hanoun | |
| 2007/0239038 A1 | 10/2007 | Nicolaescu et al. | |
| 2008/0074254 A1 | 3/2008 | Townsend et al. | |
| 2009/0069156 A1 | 3/2009 | Kurunmaeki et al. | |
| 2009/0198112 A1 | 8/2009 | Park et al. | |
| 2010/0216601 A1 | 8/2010 | Saalasti et al. | |
| 2010/0249619 A1 | 9/2010 | Kasama | |
| 2012/0029370 A1 | 2/2012 | Roecker et al. | |
| 2013/0053990 A1 * | 2/2013 | Ackland .............. | A61B 5/1123 700/91 |
| 2013/0325498 A1 * | 12/2013 | Muza, Jr. ............... | G16H 50/30 705/2 |
| 2014/0088444 A1 | 3/2014 | Saalasti et al. | |
| 2014/0278220 A1 | 9/2014 | Yuen | |
| 2014/0288448 A1 | 9/2014 | Saalasti et al. | |
| 2015/0044651 A1 | 2/2015 | Thomas | |
| 2016/0184637 A1 | 6/2016 | Pulkkinen et al. | |
| 2016/0196326 A1 * | 7/2016 | Andon ..................... | G06F 7/02 707/740 |
| 2017/0251962 A1 | 9/2017 | Shiho | |
| 2017/0258367 A1 * | 9/2017 | Cheng .................. | A61B 5/0022 |
| 2018/0174685 A1 * | 6/2018 | Hämäläinen ......... | A61B 5/0205 |
| 2019/0029586 A1 | 1/2019 | Saalasti et al. | |
| 2020/0261769 A1 | 8/2020 | Seppänen et al. | |

FOREIGN PATENT DOCUMENTS

| | | | | |
|---|---|---|---|---|
| EP | 3340248 A | | 6/2018 | |
| EP | 3391809 A1 | | 10/2018 | |
| GB | 2532745 A | | 6/2016 | |
| JP | 2011200557 A | * | 10/2011 | |
| JP | 2019166153 A | * | 10/2019 | |
| WO | WO-2007132245 A1 | * | 11/2007 | ........... A01K 11/008 |

OTHER PUBLICATIONS

Search Report issued on Apr. 28, 2020 in corresponding European Application No. 20158226.9; 8 pages.

* cited by examiner

METHOD AND APPARATUS FOR ASSESSING ACCLIMATIZATION TO ENVIRONMENTAL CONDITIONS AND TO ASSESS FITNESS LEVEL TAKING INTO ACCOUNT THE ENVIRONMENTAL CONDITIONS AND THE LEVEL OF ACCLIMATIZATION

RELATED APPLICATIONS

The present application is a continuation of, and claims priority benefit to, co-pending and commonly assigned U.S. patent application Ser. No. 16/794,466, filed Feb. 19, 2020, which itself claims priority to Finish Application No. 20195128, filed Feb. 19, 2019. The contents of each application is hereby incorporated by reference in its entirety into the present application.

BACKGROUND

Extreme environmental conditions have been shown to have an impact on fitness performance, such as in conditions of high heat and humidity or higher altitude where oxygen levels are diminished. These extreme environments can negatively affect performance because the body has not sufficiently adjusted to the conditions. It is possible for a person to adjust to the conditions but this may take spending time in the environment or even exercising in the environment before being fully adjusted. Even then, the body may not fully adapt to the conditions and performance will always be somewhat compromised.

In addition to lowered athletic performance, a person is also at risk of health problems if they are not fully acclimatized to the extreme conditions but commence training as they would normally. At higher altitudes, typical illness like colds can occur as the body is working much harder to achieve the same level of performance compared to lower altitudes, and in more extreme cases, altitude sickness can occur, which is a potentially life-threatening condition. Similarly, athletes trying to exercise in hot and humid conditions when they are not fully adjusted are at significantly higher risk of heat related illnesses compared to those who have already acclimatized.

Therefore, it is important for any exerciser to be aware of how well they have acclimatized to the new conditions they are training in, what their actual fitness level is in the new conditions, how the acclimatization process is affecting their fitness, how long they have until they are fully acclimatized, and to have training recommendations during the acclimatization process to speed up the adjustment period or maintain training while staying safe from illness or injury.

The document EP 3 340 248 A1 presents a method for determining training status and fitness level therein. It has referred to converting the calculated fitness level in hot condition to correspond normalized conditions. However, no specific method is disclosed.

SUMMARY OF THE INVENTION

The present invention discloses a system of estimating acclimatization to environmental conditions, and providing a corrected fitness level estimates based on said acclimatization level. The environmental conditions are particularly related to heat and altitude.

The current invention provides an assessment of the level acclimatization a user has achieved in environmental conditions. In this case, the extreme environmental conditions relate to extreme levels of heat and altitude. The environmental conditions may be actively monitored by a device or received before and after the exercise session. The method also takes into account a user's current physiological data and their previous training history data.

This application presents correction primarily due to heat index and altitude is secondary factor. They may exist simultaneously.

In other words, during a workout a correction factor is applied to instantaneous VO2max estimates if heat index is above 22 Celsius and/or altitude is above 800 m. Preferably correction factors decrease when the system detects that the user has acclimatized to hot conditions or high elevation, respectively. Said values 22 Celsius and 800 m are typical values and not essential values for this invention.

While this application presents a heat dose as a primary factor and an altitude secondary factor, they could be interchanged (not part of this invention), keeping the overall process quite similar. They may also exist simultaneously.

The method can be implemented in an embedded device having limited CPU and memory resources and having a host system. In one embodiment the host system uses ETE library, where the ETE is a real-time heart rate analysis library. ETE has several software modules herein, which are called and executed temporarily to calculate additional values.

In a preferable embodiment the selection of key variables minimizes the demand of resources, particularly RAM memory, and more specifically dynamic memory. The demand of resident memory is very limited, when only characteristics of each exercise and daily environmental conditions are stored.

The acclimatization calculations utilize training history data including all kinds of exercise type data. The calculation analyzes training load peaks to calculate the training data, and also takes into consideration training temperature and humidity, training altitude or living altitude. In order to optimize memory usage, there may be a 14 to 18-day training history available when calculating heat acclimatization, and a 35-day history when calculating altitude acclimatization, though the system will begin calculating those measures without any training history at all. Generally, the training history comprises 15-100, preferably 20-40 exercises.

In the case of heat acclimatization, literature has shown that full acclimatization to a hot environment takes at least 4 training days. However, the amount of acclimatization required and the intensity of the training needed to adapt in the minimum of 4 days may vary based on the intensity of the heat and humidity in the particular climate. The difference between the climate the user was formerly in and the current heat level will also affect the heat acclimatization percentage. Hotter climates or higher intensity training in hot conditions may increase the rate of acclimatization. In principle, harder exercise sessions may also increase the heat acclimatization percentage. Conversely, with no exercise, the heat acclimatization percentage may not increase at all or increase very slowly.

In the case of altitude acclimatization, a person may be able to utilize their full performance potential at a particular altitude once their body has acclimatized to the oxygen levels at that particular altitude. The acclimatization level may be represented by the altitude that a person is currently acclimatized at. As such, the acclimatization level measured in meters or feet of elevation may progressively converges on the level the person is acclimatized to. For example, each day spent at a particular altitude may increase the acclimatization level according to a predetermined function, although the function may not be linear. Some athletes may only live at higher altitude while training at lower altitudes, in which case inputting a "living altitude" may also be possible which will subsequently increase their acclimatization level.

The corrected fitness level, acclimatization, and athlete feedback may be presented in a variety of ways depending on the device being used. In addition to the raw data calculated in a fitness level value (such as VO2Max) or in a percentage acclimatization value, further calculations may be performed, such as the percentage of fitness level decrease being experienced, the time required to become fully acclimatized, the current altitude a person is acclimatized to, as well as other feedback related to adjusted fitness levels.

The following table shows some exemplary definitions and abbreviations of terms used in the exemplary embodiments described herein.

| Term or abbreviation | Definition |
| --- | --- |
| HR | Heart rate (beats/min) |
| HRmax | Maximum heart rate (of a person) (beats/min) |
| VO2 | Oxygen consumption (ml/kg/min) |
| Fitness level | Described a person's level of fitness, and may be measured, for example, via a maximum oxygen consumption (VO2max) value of or via maximum metabolic equivalent (maxMET) value of the person |
| VO2max | Fitness level, maximum oxygen consumption capacity of a person (ml/kg/min) |
| Training Load | A measure of the amount of training a person has performed, and may take various forms. One can measure training load in a single session, or cumulatively over a period of time. More or harder training will have a higher training load. |
| HRV | Heart rate variability meaning the variation in time interval between successive heart beats. The magnitude of heart rate variability may be calculated from electrocardiographic or photoplethysmographic signals, for example. |
| EPOC | Excess post-exercise oxygen consumption. As it can be nowadays estimated or predicted—based on heart rate or other intensity derivable parameter—it can be used as a cumulative measure of training load in athletic training and physical activity. |
| TRIMP | Training Impulse score. A cumulative measure of the impact of a training session |
| Heat dose | Heat dose is a metric of any kind that approximates the impact of heat exposure considering the acclimatization/adaptive benefits. |
| Sensor data | Data collected using any kind of sensor. Sensor may be in close proximity to a person such as watch or heart rate belt but it may as well be measured by any sensor which is able to communicate with a consumer device. For example, a wearable device may communicate e.g. via an mobile application with a weather service portal and extract weather information e.g. on temperature humidity, wind speed & direction, cloudiness and solar radiation while the wearable device could only measure heart rate and speed |
| Environmental data | Environmental data includes information on e.g. local temperature, humidity, wind speed, wind direction, cloudiness, precipitation, solar radiation, barometric pressure and elevation. |

Fitness Level Correction & Acclimatization Steps

The method for correcting fitness level with respect to acclimatization to extreme environmental conditions and may comprise the following steps:

1. Receiving previous training history, optionally including environmental information, including weather information or altitude information
2. Weighting each training load in history based on proximity to current date Obtaining heat dose OR training effect and heat index in each history workout
3. Determining current environmental conditions, such as temperature, humidity and altitude information, via detection using sensors within the device, from an outside source or by manually inputting for the current exercise session
4. Calculate acclimatization level by using information on current instantaneous heat index and weighted sum of heat doses of all exercises in the workout history
5. Calculate fitness level correction based on current environmental conditions and current acclimatization
6. Adjust calculated fitness level based on environmental conditions and acclimatization level
7. Provide user feedback information on fitness level and acclimatization All history parameters have been calculated in real time using a real time analysis library (ETE-library). Same ETE library may be used to obtain the history sum values to calculate current acclimatization status:

The variables required to make these calculations within ETE include each day's training load (TL) peak value, activity class value, an average heat index value during the exercise when TL peak was achieved, and e.g. average altitude value of residence. History data parameters could also be called from a separate training history analysis (THA) library which principal purpose would be calculating history summaries only when necessary (e.g. every morning after wake-up and after each training session) whereas ETE library calculates real-time results e.g. every 5 sec intervals. The method may determine a level of acclimatization, and may present all of the above-mentioned information to the user on a mobile device, such as a smartphone, or a wrist watch.

Fitness Level Correction in Heat Conditions

The heat correction of VO2Max may be based on a measured heat index, temperature, humidity, and alternatively wind chill (all from weather conditions and from movement speed). If available, heat index may be used as such, but alternatively it may be calculated based on ambient temperature and humidity values. Said values are based on weather service values provided prior to the start of the workout, or measured temperature information during the workout with device sensors if available. Heat index may be affected by windchill effect caused by both ambient wind and movement speed. In many situations, measuring only the movement induced wind chill effect will increase the accuracy of "effective heat index" (="heat sensation") significantly and is also efficient in terms of calculation resources. For example, cycling typically induces higher wind chill effect than running and the difference in "heat sensation" increases as the difference between speeds increases (i.e. lower "heat sensation" in cycling). By calculating the resultant cooling effect of wind by combining movement speed, movement direction, wind speed and wind direction even higher accuracy of "heat sensation" may be achieved but this also increases the use of calculation resources. Weather condition values may also be entered manually, for example in case where the device is not connected to internet weather service provider. The VO2max correction only applies when certain conditions are met. By way of example, a threshold may be 22 degrees Celsius, wherein the fitness level correction only occurs when the temperature is detected to be equal or higher than that value.

During exercise, fitness level calculations may be performed in real-time using a known real-time fitness level calculation, such as in US application U.S. Pat. No. 10,123, 730, or they may be calculated after the workout. A "heat correction factor" is calculated using a person's current training session and training history, as well as well-known tables that factor in heat and humidity, in addition to a collected database on exercise information. For each fitness level estimate as determined in the abovementioned method, the value may be corrected based on calculated heat sensation.

The correction factor is scaled to increase based on detected temperature, though the correction factor only starts at a specific temperature and may only be used after crossing a specific temperature threshold. Heat index is a well-known measurement that considers both heat and humidity which may more adequately describe the actual temperature the body is experiencing in a hot climate. When available, the calculation will initially use a heat index value. If humidity is not available, temperature may be used.

In addition to the inputs of temperature and humidity, a further input of GPS speed during exercise is also considered.

One of humans' temperature regulation mechanisms is via heat convection, wherein the movement of air carries heat away from the body. At rest, the air surrounding one's body is relatively still, while in motion, the warmer air is continuously replaced by the air in the environment the person is moving through. At faster speeds, there is more rapid air transfer around the body. When the air temperature is cooler than that of a person's skin, there is a heat transfer and a cooling effect occurs.

The effect of wind speed (wind chill factor—WC), is added to the measured temperature, for example using the following formula:

$$WC = 0.0817 * (3.71 * SQRT(\text{WIND SPEED } MPH) +$$
$$5.81 - 0.25 * \text{WIND SPEED } MPH) * (Tf - 91.4) + 91.4$$

Wind speed may be the detected windspeed based on sensors within the device or an estimated wind speed from the derived weather information, combined with the ground speed of the user.

The target of heat correction of fitness level is to achieve stable representation of user's fitness level without weather induced effects. For example, if heat correction is not to be applied, fitness level feedback in hot conditions may be discouraging (e.g. VO2max dropping from 50 to 48 ml/kg/min) even though this change may be solely induced by the hot conditions which increase heart rate levels and thus typically cause lower VO2max reading in any indirect VO2max test. The heat corrected VO2max (or temperature adjusted VO2max) on the other hand might not decrease thus allowing more truthful and neutral feedback.

6

Fitness Level Correction in High-Altitude Conditions

The altitude correction of fitness level is based on variable input of the measured altitude level. The measured altitude level may be automatically detected by a device, derived from the detection of a geographic location to get an approximate altitude level, by means of barometer measurement, or by manually inputting.

Fitness level correction may be applied once a user has surpassed 800 meters in altitude, which is a well-established level where lower levels of oxygen begin to affect athletic performance. Additionally, an upper altitude limit may also be established, such as 4000 m, based on research suggesting that exercise at this altitude is considered unproductive for fitness improvement.

Depending on the desired user experience, the altitude corrected (=altitude adjusted) VO2max may be utilized in different ways in end user devices. One embodiment is showing the altitude adjusted VO2max for the user as such. In a more comprehensive embodiment the altitude adjusted value may just be used to determine fitness level trend in order to determine for example training status of a user but the altitude adjusted value is not shown for the user. In the latter use case reduced VO2max in high altitude gives a useful indication to the user that his/her exercise capacity is reduced which may be important to know when planning activities in high altitude. On the other hand, in the same device fitness level trend may remain unchanged and thus indicate that the training performed is either maintaining or productive and the VO2max decline is solely induced by the high elevation. I.e. user understands that in short term the VO2max decline in high altitude is practically inevitable while the fitness level trend showing the altitude adjusted value may indicate that user's actual fitness has remained unchanged and there is no need to worry that training would be unproductive.

Altitude correction factor is based on applicant's empirical studies and existing research related to barometric pressure and athletic performance, and factors in the amount of time spent at altitude as well as the altitude that an athlete lives or trains in. Athletes that live and train at a higher altitude may, for example, become acclimatized faster than those who only train at high altitude.

High altitude acclimatization may also provide some recovery for VO2Max, in the form of reducing the altitude fitness level correction. At altitude, the influence on VO2max and performance may never be completely eliminated by acclimatization, and some performance level reduction is always to be expected at higher elevations. The recovery of VO2max from the first day's non-acclimatized value is usually 10-40% after full acclimatization which also gives some frames to how much VO2max correction factor must be decreased during acclimatization. In one exemplary embodiment the altitude acclimatization may reduce the correction factor to a maximum of 26% of the difference between 1 and the maximum correction factor. For example, when living and/or training history shows that person is fully acclimatized to the altitude where the training is performed, the correction factor may be reduced 26% for any given altitude (by way of example, if the correction factor was 10% and reduced by 26%, the new correction factor would be 7.4%).

The adjustment of the fitness level correction based on altitude acclimatization is also affected by the current altitude as compared to previous altitudes. Higher altitudes in history (supra-altitudes) may increase the acclimatization rate for lower altitudes and vice versa, where lower altitudes will not produce complete acclimatization to higher altitudes and will increase slower.

This adjustment also allows for appropriate pre-acclimatization if a person is progressively increasing their altitude acclimatization level, by, for example, living some weeks at 1500 meters before moving up to 2500 meters.

The following formula may be used when the 21 day history is spent at a lower altitude than that of the current altitude: 1000/(10+(current altitude−past altitude)/100).

By way of example, if the current altitude is 3000 meters, but the previous 21 days exercise history has been at 1500 m, the person will currently be 40% adapted to the altitude of 3000 m.

The rate of altitude acclimatization with all depend on how strong the altitude exposure has been in that time, particularly in terms of the length of the time spent at the specific altitude level where the time has been spent. In situations where an athlete may increase their elevation while training though living at a higher altitude, the increased altitude level gives an additional increase to acclimatization at the lower altitudes. For example, a multiplier of 1.1 may be added to each increase of 500 meters, so that athletes who are spending a day at 3000 m will experience the equivalent of 1.3 days of acclimatization to the altitude of 1500 m. Thus, a person who spends time at a higher altitude than their goal altitude will acclimatize somewhat quicker than at lower altitudes.

If both altitude and heat fitness level corrections are necessary, the calculation may take both into account by finding the product of the both of the heat and altitude correction factors.

Referring to claimed method for heat dose correction the method should be modified in certain steps in an altitude version, while the overall method is similar. Instead of heat and humidity, altitude is primarily measured and determining training effect is not needed. The correction factor regarding fitness level the high altitude and time elapsed are to be registered. An acclimatization altitude $A_a$ of day j is calculated based on the acclimatization altitude on the previous day j−1, the altitude of the day j, and the previous maximum acclimatization altitude if the altitude of day j is lower than acclimatization altitude of day j−1. The acclimatization altitude of each day is calculated using the present altitude and previous altitude in such way that acclimatization to e.g. 2000 meters happens in pre-set, e.g. 21 days when moving from sea level altitude (<800 m) to 2000 meters and staying there, or in such a way that acclimatization altitude decreases from e.g. 1500 m to 800 m in preset, e.g. 21 days and from e.g. 2000 m to 800 m in present e.g. 28 days.

The correction factor is a preset value according to a new higher altitude and it is decreasing according time elapsed.

Fitness Level Correction During Exercise—Technical Operation

During exercise, the fitness level (=VO2max or maxMET or maximal_met) estimate may be influenced by instantaneous heat sensation and altitude values, as well as by estimated acclimatization to both heat and altitude. When heat and altitude correction as well as heat and altitude acclimatization estimates are utilized, three different maxMET estimates may be calculated: heat corrected maxMET, heat+altitude corrected maxMET, and uncorrected maxMET estimates. The corrected estimates are based on uncorrected estimate multiplied by according correction factors.

Real time calculation flow during exercise may proceed as follows:

1. Exclude time periods with low expected reliability
   a. e.g. First few minutes of exercise
   b. too low external workload
2. Calculate uncorrected instantaneous maxMET e.g. according to patent U.S. Pat. No. 10,123,730 e.g. in 1-10 sec intervals at predefined time intervals
3. Calculate heat corrected and heat+altitude corrected maxMET based on instantaneous heat sensation and altitude values
4. Calculate reliability for the instantaneous uncorrected, heat corrected and heat+alti corrected maxMET maxMET values
5. Calculate unweighted values for uncorrected, heat corrected and heat+alti corrected maxMET for the exercise as a weighted sum of respective instantaneous values where the weight of each time instant may vary e.g. between 0.05 and 1.5 and where the weight is determined based on the reliability of the data using information on
   a. Stability of external workload (or external power output)
   b. Stability of heart rate
   c. coherence between internal intensity and external workload
   d. coherence between the instantaneous estimate and non-exercise-based estimate
   e. difference between background parameter estimated maximal MET and exercise data based maximal MET estimate
   f. internal intensity level
   g. instantaneous body fatigue level
   h. instantaneous internal intensity
   i. instantaneous anaerobicity
   j. training load Calculate the final weighted maxMET values for uncorrected, heat corrected and heat+alti corrected maxMET as a weighted average of background values and the values of current exercise where the weight of current exercise may increase as function of accepted measurement points and their reliabilities.

The heat correction factor is calculated based on the time weighted sum heat dose calculated during the heat acclimatization finalization. The heat acclimatization correction factor is larger than one only if current heat sensation is greater or equal to 22° C. In that case the correction factor is $$1 + 0.00487 \cdot (HI - 21) \cdot D \cdot \frac{\min(TE, 25)}{25},$$

where TE is the current training effect, HI is the heat sensation (heat index that takes also windchill effect into account), and D is the total heat history coefficient (<=1) based on the exercise history sum dose.

Training effect (TE) is included to the formula to limit the VO2max correction in easy exercises (low end TE) and more generally also during the early part of harder exercises. TE-value is meant to model the accumulation of heat load caused by exercising itself. When TE is low the heat load is lower since body does not yet have to struggle with the heat produced by itself. When exercise proceeds the heat load becomes more apparent as the body needs to handle the heat produced by exercise while the environment simultaneously challenges body's temperature regulation (e.g. less possibility to remove heat via convection and more need to lean on evaporation when compared to cold environment). When TE gets higher also the heat load of exercising per se increases. Requirement for scaling correction based on TE in real time was added based on observations made in applicants' own empiric database. That contains totally approximately 80 measurements, approximately 60 of which were performed in hot conditions. Approximately 20 measurements were control measurements in normal room temperature.

Without the TE scaling VO2max would be significantly overcorrected in easy workouts and in early parts of harder workouts.

A more general expression for the heat index may be is that it depicts an actual temperature that the body is experiencing in a hot climate due to decreased heat transfer from the body. The main factors dry temperature and humidity, but wind chill, radiation and even altitude may affect.

The altitude correction factor is based on Peronnet et al. (1991), which is a third order polynomial of the pressure at current altitude and calculated as:

Calculate pressure at altitude as Torrs using second order polynomial fit of Barometric formula $$P(a) = P_b \cdot \left( \frac{T_b}{T_b + L_b \cdot (a - a_b)} \right)^{\frac{g_0 M}{R T_b}},$$

where $P_b$ is static pressure, $T_b$ standard temperature, $L_b$ standard temperature lapse rate, $a_b$ altitude at bottom of layer b, a current altitude, R universal gas constant, $g_0$ gravitational acceleration and M molar mass of Earth's air. With altitudes less than 4000 meters layer is b=0. The values used are $P_0$=760 Torr, $T_0$=288.15 K, $L_0$=−0.0065 K/m, and a=0 m. The second order polynomial least squares fit to altitude interval [0 m, 4000 m] is $$P_{poly}(a) = 3.726 \cdot 10^{-6} \frac{Torr}{m^2} \cdot a^2 - 0.08916 \frac{Torr}{m} \cdot a + 759.7 \ Torr.$$

When the ambient air pressure is estimated for the current altitude then altitude correction factor is calculated according to Peronnet et al. (1991; based on Wilber 2004, page 29)

$$C(a) = \frac{100}{\begin{array}{c}-174.145 + 1.090 \ Torr^{-1} \cdot P(a) - \\ 1.512 \cdot 10^{-3} \ Torr^{-2} P(a)^2 + 0.727 \cdot 10^{-6} \ Torr^{-3} P(a)^3\end{array}}.$$

This correction factor is then scaled based on the altitude history and the final altitude maximal met correction factor is $$C_a(a, A_a) = 1 + C(a) \cdot (1 - 0.26 c(a, A_a) \, ),$$

where C is the Peronnet et al. correction factor and c is $$c(a, A_a) = \min \left( 1, \frac{A_a - 800 \ m}{a - 800 \ m} \right),$$

where $A_a$ is the acclimatization altitude, a is the current altitude, and the 800 m is there because acclimatization altitude is always at least 800 meters.

Heat Acclimatization Factor

As a user spends more time exercise in hot conditions, the body will eventually adapt as much as possible to the conditions. The calculation of the "heat acclimatization factor" may be calculated in, for example, a 14-18-day sliding window. A longer window typically increases the accuracy but may also increase memory requirements.

Values of selected variables of each day are recorded in a sliding window of a plurality of past days, preferably, at minimum, 14 days, the selected variables including at least the training load peak, the average temperature, and the average humidity for each training session. The memory demand and calculation time can be minimized with this selection of variables. The calculation may be run quite seldomly, usually only when a new exercise exists. Due to the low memory/CPU requirements the calculation typically takes only a couple of milliseconds.

Training load may be described using a training effect value (TE), and may be calculated based on a cumulative value of training load, particularly a cumulative value of disturbance of homeostasis brought by exercise. Such values may include, for example, excess post-exercise oxygen consumption (EPOC). EPOC is a measure depicting disturbance of body's homeostasis and therefore suitable for estimating training benefits. Applicant's prior U.S. Pat. Nos. 7,192,401 and 7,805,186 disclose a method for estimating EPOC during exercise and scaling of EPOC values to training effect values. Additional cumulative values of training load may also be used, such as TRIMP scores.

Acclimatization to heat is based on combination of training load/Training Effect achieved as well as ambient heat index of history workouts. Higher intensity sessions may therefore increase the acclimatization factor more than easier workouts. Acclimatization to heat is based both on the heat index and the calculated training load to create a heat dose value for each exercise. The heat dose of a single day may be the sum of the exercise heat doses experienced during a single day. Current heat acclimatization is calculated as a weighted sum of history heat doses where the weight of history workouts may decline if they are far in history (e.g. older than 10 days) or if successive heat doses are separated by too many days (e.g. 5 days).

The heat acclimatization factor for current and each history training session may be calculated using training history variables, using the following equation:

Heat dose=((TE*TE*(MAX(21, heat_index)−21)*10)/35)/2∧16, where TE=0–50, more generally Heat dose=$c*TE^a*ID^b$, where c=constant
TE depicts an achieved training effect in the exercise
ID depicts a calculated heat index difference during the exercise
a=1.5 . . . 2.5, preferably 2.0
b=0.8 . . . 1.2, preferably 1.0
The equation above is based on empirical modelling.
Thus, each heat dose is essentially proportional to a square of the achieved training effect in the exercise and proportional to the calculated heat index difference.

The following are example cases of how the calculation of heat correction factor may be affected by the training effect, the determined heat index, and a person's level of acclimatization.

In example case 1a, at the early point of exercise when TE-value is 1.0 (10) and heat index is 31 degrees Centigrade the heat correction factor for a totally unacclimatized person (D=1.0) would be calculated as follows:

$$= 1 + 0.00487 \cdot (31 - 21) \cdot 1.0 \cdot \frac{\min(10, 25)}{25} = 1.019$$

In example case 1b the session has proceeded to a situation where TE 3.0 (30) is reached—then the applied correction would be calculated as:

$$= 1 + 0.00487 \cdot (31 - 21) \cdot 1.0 \cdot \frac{\min(30, 25)}{25} = 1.049$$

In example case 2a, at early point of exercise when TE-value is 1.8 (18) and heat index is 40 degrees Centigrade the heat correction factor for a totally unacclimatized person (D=1.0) would be calculated as follows:

$$= 1 + 0.00487 \cdot (40 - 21) \cdot 1.0 \cdot \frac{\min(18, 25)}{25} = 1.066$$

In the example case 2b exercise session has proceeded to a situation where TE 2.5 (25) is reached—then the applied correction would be calculated as:

$$= 1 + 0.00487 \cdot (40 - 21) \cdot 1.00 \cdot \frac{\min(25, 25)}{25} = 1.0925$$

In example case 3a, at early point of exercise when TE-value is 1.8 (18) and heat index is 40 degrees Centigrade the heat correction factor for a fully acclimatized person (D=0.78) would be calculated as follows:

$$= 1 + 0.00487 \cdot (40 - 21) \cdot 0.78 \cdot \frac{\min(18, 25)}{25} = 1.052$$

In the example case 3b exercise session has proceeded to a situation where TE 2.5 (25) is reached—then the applied correction would be calculated as:

$$= 1 + 0.00487 \cdot (40 - 21) \cdot 0.78 \cdot \frac{\min(25, 25)}{25} = 1.072$$

In example case 4a, at early point of exercise when TE-value is 1.8 (18) and heat index is 40 degrees Centigrade the heat correction factor for a person with a 50% acclimatization level (D=0.89) would be calculated as follows:

$$= 1 + 0.00487 \cdot (40 - 21) \cdot 0.89 \cdot \frac{\min(18, 25)}{25} = 1.059$$

In the example case 4b exercise session has proceeded to a situation where TE 2.5 (25) is reached—then the applied correction would be calculated as:

$$= 1 + 0.00487 \cdot (40 - 21) \cdot 0.89 \cdot \frac{\min(25, 25)}{25} = 1.082$$

The correction factor may be applied instantaneously as the heat index may also change rapidly as e.g. wind chill effect may increase or decrease rapidly due to e.g. a changing cycling speed. If measured uncorrected instantaneous VO2max estimate is 50 ml/kg/min in the example case 4b then the heat corrected VO2max estimate for that time instant would be 50*1.082=54.1 ml/kg/min.

The maximum value total heat acclimatization factor may reach is 0.22, which 100% acclimatization to the current heat. The level of heat dose for a single day may also be limited. Daily acclimatization may be capped at a value of 0.055, or 25% of the maximum acclimatization. The amount of heat dose, when expressed in relative terms, may be limited to 125% of the daily maximum and to 100% of the daily maximum after the time decay.

A weighting system may scale the resultant correction based on the measured training effect of the workout. Easier workouts may not be impacted by the heat as much as high-intensity workouts, and therefore the estimated fitness level may be reduced less. In a workout where the intensity of the exercise is measured using "training effect", when the exercise has just started and the estimated training effect is "0", the correction factor may also have a weight of zero. Subsequently, as the training effect score increases over the duration of the workout, the weighting factor increases. An exerciser achieving a training effect of higher than 2.5 (note that in code formulas TE values are multiplied by 10 meaning that this value in formulas is 25) would then have their corrected factor fully weighted, with a value of "1". The weighting factor is a progressive measure so that training effect values in between may have their fitness level only impacted somewhat by the fitness level corrections. The purpose of load limit is to mimic body temperature during exercise. For example, a hot weather alone does not increase body temperature and doesn't therefore significantly increase heart rates before a certain load (or training effect) has been accumulated. If full correction would be used from the very beginning of exercise, then early VO2max estimates would be overestimated.

Because the heat acclimatization requires a certain amount of exercise within an approximately two-week window to become fully acclimatized, there is also a decay in acclimatization if an insufficient amount of exercise at elevated heat occurs. Depending on the amount of heat acclimatization that has already occurred and the intensity of the previous workouts, the decay in acclimatization may begin to occur as early as 3 days after the previous work. The acclimatization decay will linearly decrease over the period of the 14-18 day (much longer windows could be used as well which increases acclimation level accuracy but also increases memory requirements) sliding window if none of the previous workouts contain exercise in conditions that elicit a heat correction response.

The proximity of the days in which the training has occurred from the present day also affects the weighting of the acclimatization factor of that particular day. During the decay process, acclimatization days that occurred, for example, 10 days ago, will have less of an impact that the workout that has occurred yesterday. The equation for this history weight may be:

History weight of previous days may be calculated as=1–0.0833*(date_diff–3); where date_diff is the timely difference (in days) of the history day from present day In addition to providing a heat acclimatization value, the level of acclimatization may also affect fitness level correction. The calculated heat acclimatization factor decreases the heat correction factor as the user becomes acclimatized.

The invention is implemented in a portable device with a heart rate sensor, with the device having a processor, a memory containing runtime and resident memory, and software. Depending on type the device has an altitude sensor, GPS or a chosen interface fetching weather information (temperature and humidity) e.g. from the internet.

The method relating to acclimatization due to altitude may comprise the following steps: providing previous training history into resident memory comprising plurality of day records, optionally including environmental information, including weather information, where each day record comprising a date stamp and information regarding altitude and optionally temperature and humidity providing training history comprising timestamp and data about training load from executed exercises in stored records during each exercise carrying out periodically the following steps:

determining frequently current environmental conditions, particularly altitude by a sensor or by manually inputting for the current exercise session and storing obtained environmental information into memory, measuring continuously heart data using the heart rate sensor and storing heart rate data into a memory, determining continuously external workload data using a sensor or inputting manually and storing external workload data into a memory, determining basic fitness level value based on stored heart rate data and external workload data and training history, calculating correction factor regarding fitness level value, preferably in daily basis, based on stored altitude data of said stored records and storing the obtained factor into memory.

correcting basic fitness level value with the correction factor and obtaining a real fitness level value, adjusting stored correction factor periodically based on elapsed time, presenting the real fitness level value using the portable device.

A day record may be split into shorter periods.

Preferably, each training load in history is weighted based on proximity to the current date in order to emphasize the most recent data.

On the other hand, the method relating acclimatization due to heat dose may comprise the following steps: providing previous training history into resident memory comprising a plurality of exercise records, including environmental information, including temperature information, where each exercise record comprising a date stamp and information regarding training load, preferably training effect (peak), temperature and humidity, and preferably windchill and altitude, during each exercise carrying out periodically the following steps:

determining frequently current environmental conditions, particularly by a sensors or by manually inputting for the current exercise session and storing obtained environmental information into memory, measuring continuously heart data using the heart rate sensor and storing heart rate data into a memory, determining continuously external workload data using a sensor or inputting manually and storing external workload data into a memory, determining basic fitness level value based on stored heart rate data and external workload data and training history, calculating correction factor regarding fitness level value, preferably on a daily basis, based on stored training history including temperature and optionally humidity and storing the obtained factor into memory, correcting basic fitness level value with the correction factor and obtaining a real fitness level value, adjusting stored correction factor periodically based on executed exercises, presenting the real fitness level value using the portable device.

BRIEF DESCRIPTION OF THE FIGURES

Advantages of embodiments of the present disclosure will be apparent from the following detailed description of the exemplary embodiments. The following detailed description should be considered in conjunction with the accompanying figures in which the figures may show exemplary embodiments of the method and apparatus for assessing acclimatization to environmental conditions and to assess fitness level taking into account the environmental conditions and the level acclimatization. Figures are only exemplary and they cannot be regarded as limiting the scope of invention.

Correction factors are calculated in both prongs, step 17. Altitude-correction is based on time elapsed while at altitudes over 800 m. Heat dose correction is based both training and heat dose history.

When correction factors are calculated they can be applied in the fitness level calculation and obtain final workout values (step 19) for corrected fitness level, 18. Finally the result is added to history, step 20. The results are added to history, step 21 and the execution returns back to step 10 above.

Figure 1:
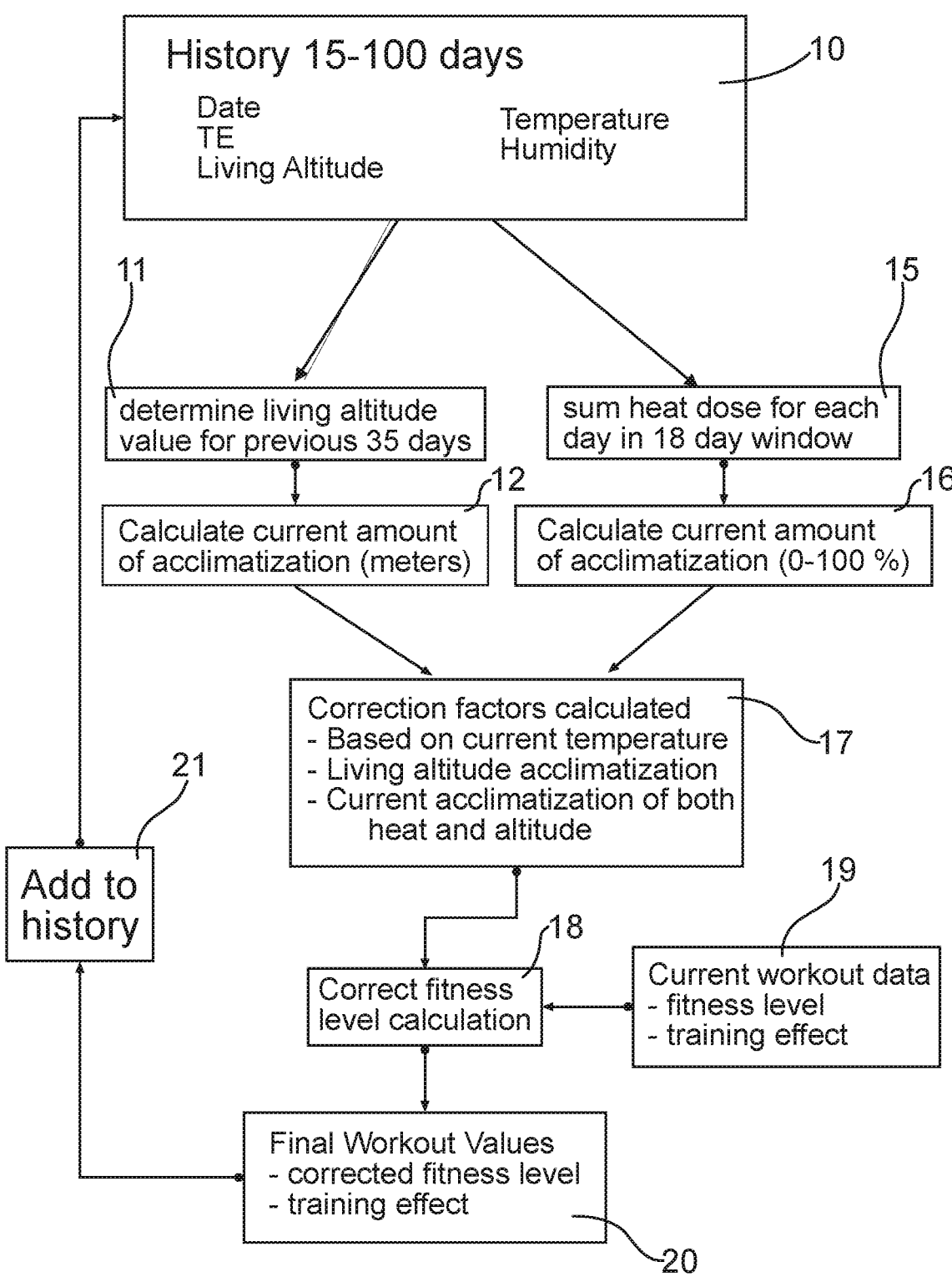
FIG. 1 represents a flowchart visualizing the process of determining amount of acclimatization both due to altitude and heat exposure
Figure 2A:
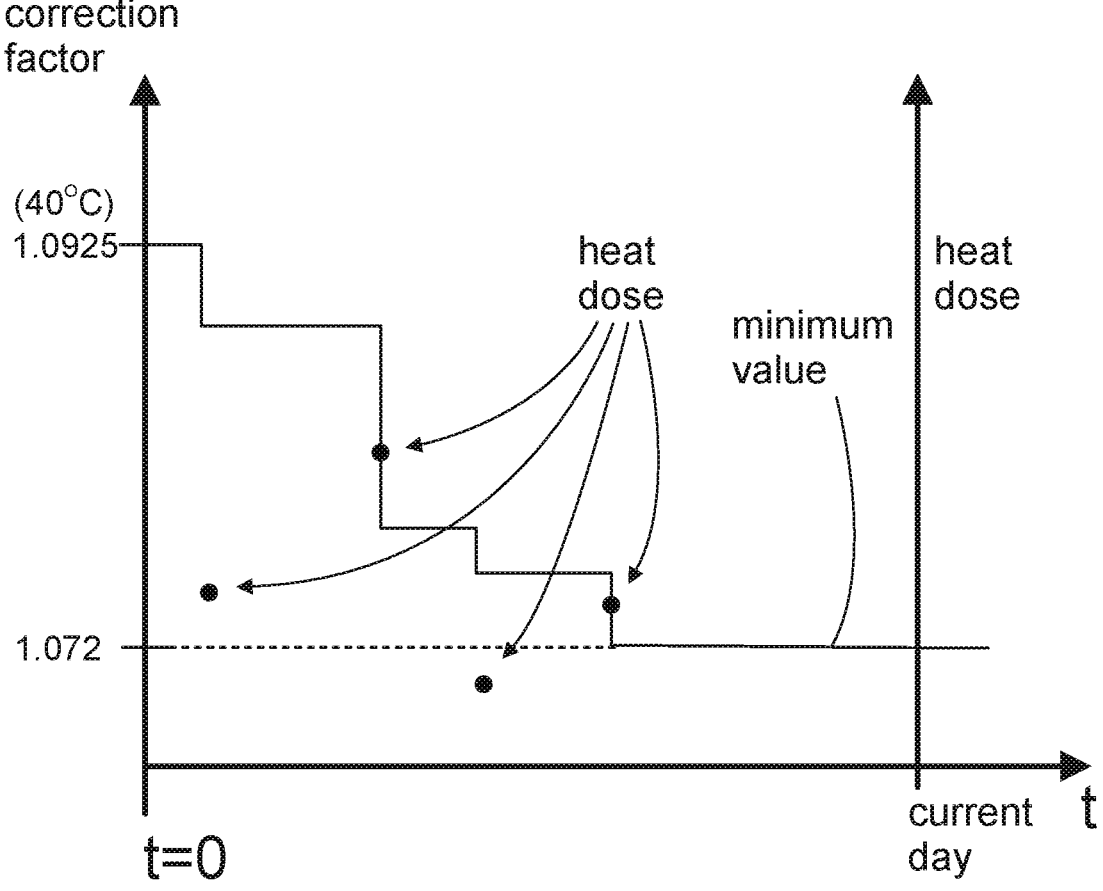
FIG. 2a represents an illustration of typical acclimatization process in hot climate

In hot climates the correction factor is set initially to a value based on ambient heat index. As shown in FIG. 2a, where an exemplary initial correction factor is 1.0925 as a starting point according to an heat index of 40° C. By performing exercise in the heat, the body gradually adapts to the hot climate, depending on the heat dose of each exercise. A heat dose depends on the training effect gained in the exercise and the ambient heat index. The greater a training effect and/or heat index in the exercise the bigger the induced heat dose. Finally when the body is fully adapted to hot climate the correction factor does not decrease anymore, and the minimum correction factor (1.072 in 40° C.) is reached.

Figure 2B:
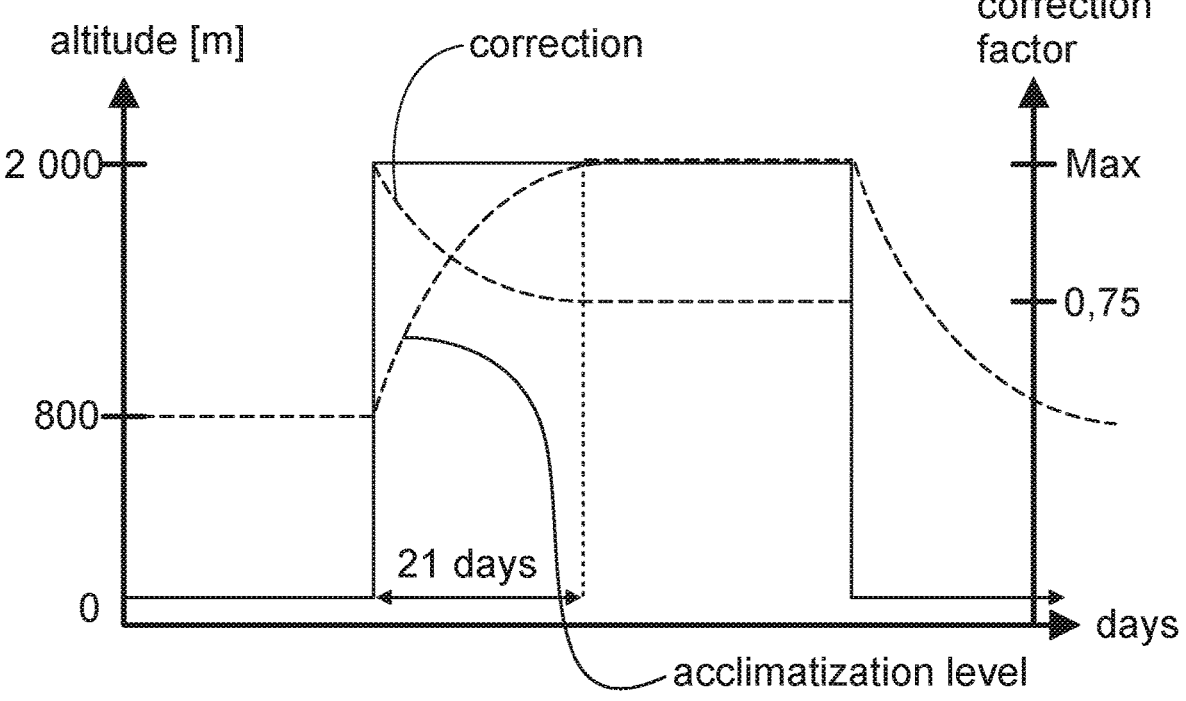
FIG. 2b represents an illustration of typical acclimatization process when changing altitude

FIG. 2b shows the acclimatization process when a user lives at 2000 m altitude for a few weeks and then returns back to sea level. After arriving at 2000 m the acclimatization is low and it takes 21 days to adapt fully to that altitude. Respectively the correction factor is biggest on the date of arrival and decreases in 21 days to value of 75% of the maximum value.

After retuning back to the sea level acclimatization returns in few days back to normal (800 m). User gains temporarily benefit, but that disappear in 1-2 weeks.

Figure 3:
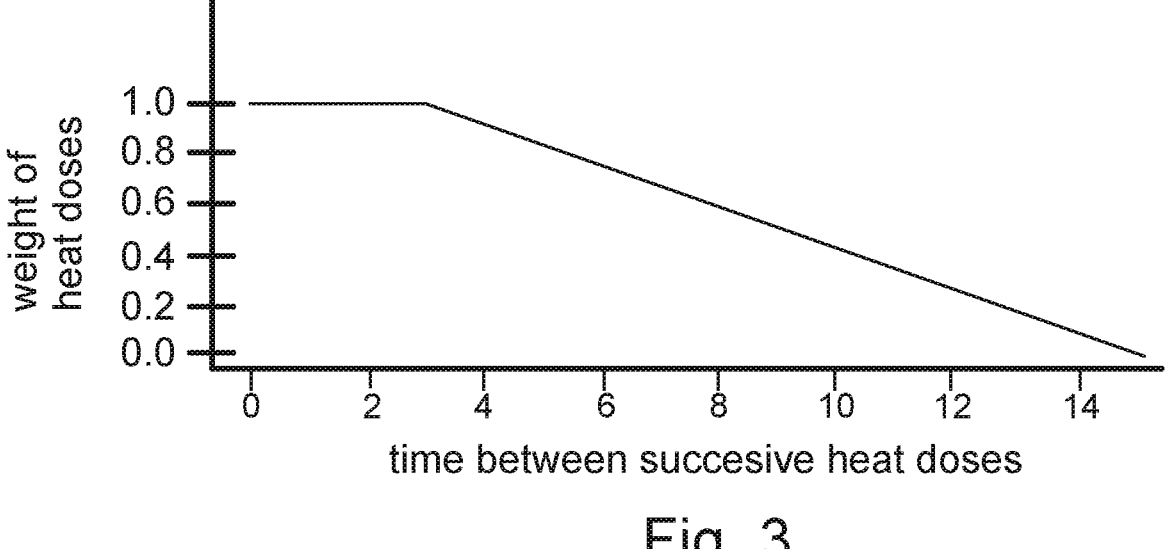
FIG. 3 represents example of reducing weight history heat doses

FIG. 3 shows an example of the weighting value during a 15 day heat dose history where the values for today's (on day x) workout gets 1.0 and the weight remains at 1.0 between days x−1 to x−3 but starts to decrease towards zero after that. The decrease always occurs when there is a gap longer than 3 days in heat exposures. In cases when there is a training session today and 15 days ago, today's workout would get a weight of 1.0 and the 15 day old session would get a weight of approximately 0.08.

In addition to this logic the weight of older (e.g. older than 10 days) measurements may be reduced even if heat exposure workouts are repeated every day or every other day, for example. By this way acclimatization value may behave more smoothly as the oldest days dropping out of history would not have so a big effect on current acclimatization status.

Altitude Acclimatization

Altitude acclimatization is calculated using a 35-day training history, and may consider both training altitudes and living altitudes. Upon initialization of a measurement, values in specific variables for the previous 35 days are input. Measurements older than 35 days may be ignored.

The altitude acclimatization level is provided as an absolute altitude level to which a person is acclimatized. Altitude acclimatization level can be also higher than current altitude level—in cases when person goes to lower altitudes which allows user to assess his/her readiness to return to higher altitudes as well as to see the decay of the physiological benefits during low altitude residence. When the current altitude and the altitude acclimatization level are the same (or if acclimatization level is higher than current altitude), then the person is able to utilize their full performance potential at that altitude.

For each day within the 35-day training history, an altitude value is input when a measurement is initialized. The altitude value may be derived via the device's GPS, barometer, Wi-Fi, or cellular signal detection, or by other normal means within a technological device. A person's current location (such as the city they are currently in), may also be put in manually to get a general estimate of altitude, or the altitude itself may be input manually.

Altitude acclimatization may output an absolute altitude level to which a person is acclimatized. It is typically represented in meters, though it may reasonably be converted into other units of measure, such as feet.

The altitude acclimatization measurement may initially use living altitude, when available. Devices that can acquire altitude, such as wearable devices, watches or wristop computers, mobile phones, may be able to take an average of altitudes during non-exercise time to assess a person's living altitude. In one embodiment—while reading the history data-living altitude values may be differentiated from training altitude values based on training load. Living altitude values can be recognized by looking at corresponding training load peak which should be 0 or close to 0 whereas any appropriate training session will accumulate load approximately 10-300 units or even more.

If living altitude is not available, the method may instead use an average altitude from the most recent training session. If there is no altitude measurement for some day in history, either in training or in living altitude, then the acclimatization calculation, on initialization of a new measurement, may use the last measured altitude value from the history for that day, which may be either a living or training related value.

The altitude acclimatization level is also associated with the fitness level altitude correction as described above, where when altitude acclimatization increases a person will have lower altitude correction for VO2max for any given altitude.

If a person goes down from a higher altitude to a lower altitude, then their acclimatization to altitude will slowly decay. Therefore, with continued acclimatization calculations, the system will re-adjust a person's altitude acclimatization to a lower altitude. The decay of altitude acclimatization depends on the altitude level and the amount of time spent there. The longer one spends at altitude and the higher the altitude is, the longer period of time it takes before a person to return to normal. For example, a person who is fully acclimatized to 1500 meters may return to normal in 21 days, while a person acclimatized to 2000 m or more may take up to 28 days. This is in line with (high altitude) training physiology where some functional adaptations may appear rather quickly during a short and/or moderate altitude exposure but they also disappear quickly whereas longer residence in high altitude brings up also structural changes in body which also disappear more slowly.

Presentation of acclimatization level to a user may be in a percentage of value, where 100% represents a user being as acclimatized as a normal human can be to the conditions. Alternatively, the acclimatization value may be given in meters, representing the altitude at which the user is currently acclimatized to. If an athlete is living at 1500 m, for example, and they have been determined to have been acclimatized to a level of 1000 m, they can reasonably assume if they went down to that altitude, they will be sufficiently acclimatized at that level.

Heat & Altitude Acclimatization in ETE

The API elements in ETE for acclimatization calculations are
   ete_history_exercise struct, which contains the necessary information about an exercise performed earlier.
   ete_add_exercise function for adding past exercise information
   ete_input struct, which contains some variables related to acclimatization ete_analyze function, which advances the analysis ete_results struct, which contains some variables that are needed to form the ete_history_exercise struct of the ongoing measurement ete_get_results functions, which reads the current results into a ete_results struct ete_get_acclimatized_altitude_meters function, which returns the current acclimatization altitude ete_get_acclimatized_heat percentage function, which returns the current heat acclimatization percentage ete_get_days_to_full_acclimatization function, which returns the days needed at a target altitude to reach full acclimatization.

The order in which the API functions must be called is
1) ete_set_parameters to reset ETE
2) ete_add_exercise for all past exercises
3) all other functions in desired order.
ete_add_exercise function This function takes one ete_history_exercise struct and adds the information of that exercise to the internal state of ETE.

If the training_load_peak field in is zero, the ete_history_exercise is not an actual exercise, it only contains information of the altitude the user is staying at that moment. This living altitude is used as the primary source of altitude information. If training_load_peak>0 the ete_history_exercise is a true exercise. Living altitudes and history altitudes are saved into separate arrays at this moment.

Also, the effect of the temperature and humidity of this exercise is calculated and saved into an array. For each exercise the heat index based on temperature and humidity is calculated. If humidity is not available, temperature is used instead of heat index. If temperature is not available, the heat dose of the exercise is zero. If heat index (or temperature if humidity not available) is under 22° C., heat dose is zero. Otherwise, heat dose of the exercise $C \times (TE*TE*(HI-21)''$, where C is constant depending on the units used therein.

where TE is training effect of the exercise in range [0, 50], HI is the heat index (or temperature if humidity is not available). The heat dose of each day is the sum of the heat doses of the exercises on that day limited to 125% of the daily maximum dose 0.055, 1.25*0.055=0.069.

After all (at maximum 35 previous days is used) history exercises are given with this function, any other function can be called.

Calling any relevant function (ete_analyze, ete_get_acclimatized_altitude_meters, ete_get_acclimatized_heat_percentage, ete_get_days_to_full_acclimatization) after all history exercises are fed to ETE will trigger a finalization of the acclimatization history calculations.

Living and exercise altitudes are at this point in two separate arrays. For each day in the living altitude array starting from the oldest:

1) If there is living altitude for this day, move to the next day
2) If there is exercise altitude, fill this day's living altitude array value with the exercise altitude and move to the next day
3) Fill this day's living altitude array value with previous day's value.

In short, the principle is to use primarily current day living altitude, secondarily the current day exercise altitude, and assuming that the user stayed at the same altitude if no new information is given.

After the altitude history array is filled, we can calculate the current acclimatization altitude. The acclimatization altitude is initialised to 800 meters, and for each day in the altitude history that day's altitude changes the acclimatization altitude. The change is calculated as follows:

if altitude is higher than on the previous day, a=0.18 using this multiplier, full acclimatization takes place in about 21 days. The absolute rate of acclimatization is fastest in the beginning of high altitude residence and slows down over time.

if altitude is lower than on the previous day, a depends on the highest altitude before the decrease started.

The dependence is a piecewise linear function [0 m, 1500 m, 2000 m, inf]->[0.18, 0.18, 0.07, 0.07].

The acclimatization altitude $A_a$ of day j is calculated based on the acclimatization altitude on the previous day j−1, the altitude of the day j, and the previous maximum acclimatization altitude if the altitude of day j is lower than acclimatization altitude of day j−1. The acclimatization altitude of the day j is $$A_{a,j} = \min(A_{a,j-1} - 15, b \cdot \max(800 \text{ m}, a_j) + (1-b) \cdot A_{a,j-1}),$$

where coefficient b is selected is such a way that acclimatization to 2000 meters happens in 21 days when moving from sea level altitude (<800 m) to 2000 meters and staying there, or in such a way that acclimatization altitude decreases from 1500 m to 800 m in 21 days and from 2000 m to 800 m in 28 days. The length of the altitude history used may affect the coefficient b. For example in a case where the user has been at 2000 m for 21 days and after that at 0 m for 21 days, but the altitude history is 35 days long, calculating the acclimatization altitude using the above equation starting from the oldest day in the history, the acclimatization altitude will not reach 2000 m at day 14 of the history, which is the last day at altitude 2000 m. After that the acclimatization altitude starts to decay because user is at 0 m and this has to be considered in the values of coefficient b or by using a longer altitude history.

The new acclimatization altitude AA_new is: AA_new=a*A+(1−a)*AA_old, where A is the maximum of current altitude and 800 m, and AA_old is the acclimatization altitude before this change.

For example, if a person has reached a acclimatization level of 1450 meters on day X and if that day is spent at sea level then the new acclimatization value at day X+1 may be calculated as 0.18*800+(1−0.18)*1450=1333 meters.

Or, if a person has reached a acclimatization level of 2050 meters on day X and if that day is spent at sea level then the new acclimatization value at day X+1 may be calculated as 0.07*800+(1−0.07)*2050=1963 meters.

Accordingly, minor acclimatization benefit may be implemented to decay faster than more significant acclimatization benefit.

To summarize, these exemplary formulas allow acclimatization level to follow a pattern of typical physiological acclimatization and acclimatization decay processes where both the acclimatization as well as the decay are fastest in the beginning and slow down over time. Furthermore, using these exemplary formulas, higher level of adaption reflects more permanent acclimatization; i.e. higher amount of structural adaptations, which also decay more slowly than less significant adaptations.

The following example discloses one possible embodiment to calculate history heat dose in a way that takes the physiological decay of adaptation into account: First, it may be checked whether there has been a day with heat dose that is no more than three days old. If such a day is found, examination may start from that day, otherwise it will start from the current day. The algorithm may then check backward in the heat dose history day by day. At first a coefficient c=1 may be used. The algorithm browses backwards through the history and for days that have a heat dose, it calculates how large a gap there was between the heat doses. If the gap is larger than three days, coefficient c gets multiplied by 1−0.083*(gap−3), i.e. it reduces 8.3% for each day of the gap larger than three days. The final heat history coefficient D is:max(0.778, 1−sum_j(min(0.055, c_j*d_j))), where 0.055 is the daily maximum heat dose, c_j is the coefficient at day j, and d_j is the heat dose of the day j limited to 125% of the daily maximum.

Altitude is used to determine the altitude correction factor of maximal MET. Also, the mean altitude of the exercise and EWMA altitude with 5 minute effective window length are calculated. The mean altitude is given as an output and is also used in the averaging of background parameter maximal MET and current exercise maximal MET. The EWMA altitude may be used in the flag feature as the current altitude. It may be used instead of the input altitude to avoid the altitude flag from changing too rapidly.

If both input temperature and speed are given, temperature is under 32° C., and speed in under 6.459 km/h, a wind chilled temperature:

$$T\_C=0.0817*(-0.25*v+3.71*sqrt(v)+5.81)*(T\_O-91.4)+91.4,$$ where T_C is the corrected temperature in Fahrenheit, v is speed in miles/hour, and T_O is the input temperature, is calculated.

The mean wind chilled temperature and mean humidity of the exercise as well as heat dose are calculated and given as output.

The heat index is calculated from the wind chill corrected temperature and the humidity. It may be calculated according to Meteorology for Scientists and Engineers by Stull & Ahrens. If only temperature is available, temperature may be used instead of the heat index. The heat index is used to determine the heat correction factor of the maximal MET. Heat index uses only the dry bulb temperature, so no radiation component is taken into account. The wet-bulb globe temperature (WBGT) would be a more accurate measure of the apparent temperature, but it is more complicated to calculate. It should be obvious for a person skilled in art that any measure of heat sensation (WBGT, humidex, wind chill corrected heat index etc.) may be used, though the algorithm should be optimized for each given heat sensation index to maximize the accuracy.

Resultant Calculation Values and Possible Additional Applications

The above-described calculations would result in at least in the following variables available:

Fitness level corrected based on heat
Fitness level corrected based on altitude
Updated heat dose history
Updated altitude dose history
Current acclimatization level in meters
Current heat acclimatization in percentage of full acclimatization
Number of days to target altitude acclimatization These variables may be presented to a user as is on an apparatus such as a smartphone or watch, or may be used in forward calculations, such as modification of race time predictions, next workout recommendations, recovery states, training statuses, or the like, where fitness level play a role in the calculation. The data may also be added to a training database to be recalled in a future calculation.

Example Processes of ETE Library Function

Heat acclimatization percentage (ete_get_acclimatized_heat_percentage)

Tells as a percentage (0-100) the level of person's heat adaptation. I.e. The readiness to train and compete in heat Is calculated using a 15 day training history taking into account training load peaks as well as training temperatures and humidities Obtain training_load peak, average_temperature and average_humidity from ete_results struct for each session and input these values as an ete_history_exercise struct at least from last 15 days when initializing each measurement Taking these values from ETE results is recommended since the average_temperature already takes also the windchill (based on movement speed) effect into account After adding the history, heat adaptation percentage can be retrieved with ete_get_acclimatized_heat percentage function.

In principle—the harder the training session and the hotter the climate—the greater the increase in heat adaptation percentage No matter how hard the training is or how hot the environment is—full adaption takes at least 4 training days. On the other hand, percentage does not increase at all if no training is performed.

The feature has a decay logic meaning that percentage generally declines if there are more than 3 days in-between successive heat exposures When heat adaptation percentage increases a person will have lower heat correction for VO2max for any given temperature

Altitude Acclimatization Level (Ete Get Acclimatized Altitude Meters)

Tells an absolute altitude level (in meters) to which a person is acclimatized.

For example, if a user/athlete is acclimatized to competition altitude (i.e. if competition altitude is 1500 m and get_altitude_acclimatization_meters also shows 1500 m or close to it) then he/she is able to utilize his/her full performance potential whereas non-acclimatized person cannot—Non-acclimatized person can improve his/her performance in high altitude by staying in high altitude for a longer time so that acclimatization reaches competition altitude.

Is calculated using a 35 day training history taking into account living or training altitudes input altitude values from last 35 days when initializing each measurement. Measurements older than 35 days will be ignored even if they are input to ETE.

After adding the history, altitude adaptation meters can be retrieved with ete_get_acclimatized_altitude_meters function.

Host to input living altitude (acquired directly from watch or via connection to phone) whenever that is possible In cases when living altitude cannot be acquired average_altitude from last training session is used ETE recognizes and selects living altitude values based on corresponding 0.0 training_load_peak-value on a daily basis whenever that is possible If a person has not trained on a given day—and if the day does not include living altitude measurement either—then calculation uses last measured altitude value from the history (that may be either living or training related value)

When altitude acclimatization level increases a person will have lower altitude correction for VO2max for any given altitude

VO2Max Values in ETE maximal_met[0]=VO2max with heat correction
this one is shown for the user
maximal_met[1]=VO2max with heat and altitude correction
this one is utilized in determining VO2max trend (arrow shown for a user) and in determining Training Status
I.e. high altitude user may see "Fitness ↑" although VO2max-number is declining
maximal_met[2]=VO2max without corrections. Used only in internal calculations.

Training Alerts/Flags

As a result of the above described calculations of both heat and altitude correct fitness values and acclimatization measures, the method may also implement a notification system that flags/informs a user when their performance is affected by the conditions or incomplete acclimatization. The acclimatization flag feature informs the user if the acclimatization process is still ongoing.

Each of the flags will appear and notify the user when certain conditions are met, as described below:

Flag 0=No flag

Flag 1=Heat flag—A heat flag may appear when there is a fitness level correction to due high heat but acclimatization is below the maximum heat acclimatization factor value.

Flag 2=Altitude flag—An altitude flag may appear if acclimatization to the specific high-altitude value is not yet complete. E.g. If a user moves higher than what they have currently been acclimatized to.

Flag 3=Heat and altitude flag—This flag will appear if both of the above flag's criterion are met and may come with additional warnings and feedback regarding safe exercise levels.

Optionally, other conditions could be added to include additional flag warnings, such as notifications related to abnormally extreme heat or high altitude, irrespective of an athlete's acclimatization levels. "Flagging", as referred to above may be flexible in presentation to a user, and may be represented in a variety of notifications or alerts. Additional information that may be presented to the user is only limited to the type of device being used and the available space.

Referring to acclimatization alerts, a resolution value may be applied to workouts to prevent a premature flag alert. Relative to the currently acclimatized altitude, even it is very high, will only appear if it is again significantly higher. For example, if a resolution value is set to 300 meters, when a person is acclimatized to 2500 meters, the altitude flag will only appear after exceeding 2800 meters in altitude. Altitude acclimatization level can be calculated based on history data. This history-based value may be compared, for example, against EWMA (exponentially weighted moving average)

altitude that is measured in real time. This may allow more stable feedback if the flag/warning is used in real time.

Accordingly, the heat and altitude alerts may appear and disappear based on the current conditions within a current workout, if the ability to detect either altitude or temperature is available. This may be relevant, for example if the temperature increases throughout the day. In another example, even in an individual workout, altitude may change significantly if, for example, a person is climbing a mountain.

Technical Operation of the Flag Feature

With respect to the heat flag, if the final heat history coefficient D has not reached the minimum value 0.778 (=heat acclimatization percentage<=100%) and the user is exercising at a high temperature, the heat flag may be activated.

The altitude flag feature may have a specific logic that differs from calculation of altitude acclimatization level. The flag may be optimized to only check whether a person is ready to train normally at a given altitude level. Typically, normal training ability is reached faster than a maximum performance at high altitudes. Training ability may correlate with completion of certain functional adaptations, such as increased ventilation in high altitude and is typically achieved in a few days, whereas maximum adaption to high altitude also requires structural adaptations (such genesis of new red blood cells to improve bloods oxygen transport capacity) which may take a matter of weeks. Accordingly, this feature may be modelled to align these functional adaptions and thus to react faster to changes in elevation. This kind of feedback may be vital for a user to be able to avoid acute mountain sickness or overtraining when going to higher altitudes.

The calculation of how many days the altitude flag will remain on ("days on") may be based on altitude "bins", and number of days in the bins in the history decides if the flag is raised. There may be 7 bins, and they may be formed based on current altitude (CA) in such a way that (CA−300 m) is a lower limit of a bin, and bin widths are 500 m. The highest altitude bin may be in some cases 600 m wide to ensure there are always exactly 7 bins. First, an initial requirement for days spent at current altitude to remove the flag is calculated: [800, 1000, 1500, 2000, 2500, . . . ] meters->[1, 1, 2, 3, 4, . . . ] days.

The effect of each day in the altitude history may be summed into a corresponding bin. More distant history may be given less weight than newer history. For example, the effect may be 1 for days that are newer than (initial requirement+days already at current altitude bin). After that the effect may decays exponentially to a base value of 0.02. Each bin sum can be at maximum the initial requirement.

Next each bin may get a correction based on its height relative to the current altitude bin, which is being referred to here as "compensation days". Days at bins higher than the current altitude may get multiplied by 1+N/10, where N is how many bins higher that bin is than the current altitude bin, e.g. a bin 2 bins higher gets multiplied by 1+2/10=1.2. Days at current altitude bin may remain the same (=no correction). Days at bins lower than the current altitude may get 1 reduced from them for each bin they are lower than the current altitude bin, e.g. a bin 2 bins lower get 2 reduced from its sum. If the sum of these corrected bin sums is less than the initial day requirement, the altitude flag will still be raised. This calculation may be represented by the formula:

$$\text{days on} = 2*(\text{current\_alti\_km} - 1) + 1 - (\text{compensation days})$$

The following example illustrates the calculation of compensation days and the resultant days on. If a person has an otherwise empty altitude history (or has remained at sea level) but has then spent 3 days at 1500 m and after that 2 days at 3900 m and then goes to 3000 m altitude then "days on" for the flag is calculated as $$2*(3-1)+1-\text{compensation days}=5 \text{ days}-\text{compensation days.}$$

For this case calculation of the compensation days is illustrated in the following table:

| Altitude bin | Days at that bin | Weighted sum of days |
|---|---|---|
| 800-1200 | | |
| 1200-1700 | 2 days at altitude that is 3 bins lower than current altitude | $=\max(0; 2\text{-}3) = 0$ |
| 1700-2200 | | |
| 2200-2700 | | |
| 2700-3200 (current altitude bin) | | |
| 3200-3700 | | |
| 3700-4000 | 3 days at bin that is 2 bins higher than current altitude | $=3*1.2 = 3.6$ |
| weighted sum of compensation days | | 3.6 |

Accordingly, "days on" for the flag for this case would be:

$$2*(3.0 - 1) + 1 - 3.6 = 1.4 \text{ days.}$$

The user is warned with the flag for 1,4 days if he stays at 2700-3200 m altitude level for the coming days. Warning feedback may be phrased for example as: "Be aware that your body is not ready to tolerate normal training load due to incomplete adaption process."

The time decay is selected in such a way that staying at initial requirement amount of days at that altitude will always remove the flag exactly after initial requirement days if there is no other altitude history.

Example Implementation

The system and method according to the exemplary embodiments can be applied in many kinds of devices as would be understood by a person of ordinary skill in the art. For example, a wrist top device with a heart-rate transmitter, a mobile device such as a phone, tablet or the like, or other system having CPU, memory and software therein may be used.

Figure 4:
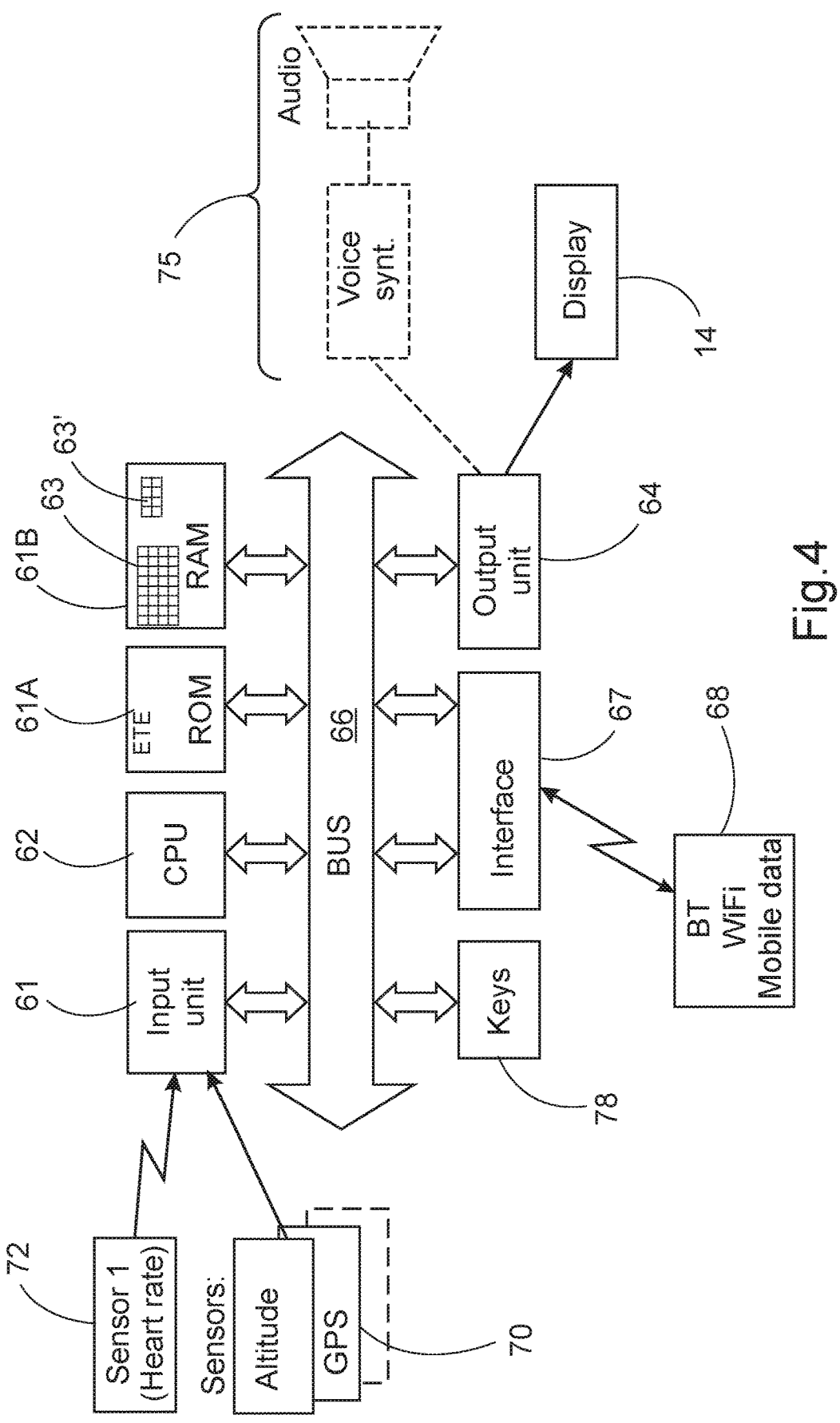
FIG. 4 represents an example of a hardware assembly.

According to exemplary FIG. 4, the implementation may include an assembly built around a central processing unit (CPU) 62. A bus 66 may transmit data between the central unit 62 and the other units. The input unit 61, ROM memory 61A RAM memory 61B including a dedicated memory 63' for the application and memory 63 for the host system, keys 78, Terminal connection 67, and output unit 64 may be connected to the bus.

The system may include a data logger which can be connected to cloud service, or other storage as would be understood by a person of ordinary skill in the art. The data logger may measure, for example, physiological response and/or external workload.

A heart rate sensor 72 and any sensor 70 registering external workload may be connected to the input unit 61, which may handle the sensor's data traffic to the bus 66. In some exemplary embodiments, the terminal or node 68 (BT=Bluetooth, WiFi, Mobile Data) may be connected to an interface connection 67. Temperature and humidity data on daily basis can be brought from the Internet (weather report/forecast data). Any connection to the Internet may be applied.

The output device, for example a display 14 or the like, may be connected to output unit 64. In some embodiments, voice feedback may be created with the aid of, for example, a voice synthesizer and a loudspeaker 75, instead of, or in addition to the feedback on the display. The sensor 70 which may measure external workload may include any number of sensors, which may be used together to define the external work done by the user.

More specifically the apparatus presented in FIG. 4 may have the following parts for determining an acclimatization factor:

a heart rate sensor 72 configured to measure the heartbeat of the person, the heart rate signal being representative of the heartbeat of the user;

optionally at least one sensor 70 to measure altitude and/or an external workload during an exercise, and a data processing unit 62 operably coupled to the said sensors 72, 70, a memory 61A, 61B operably coupled to the data processing unit 62, the memory may be configured to save background information of a user, for example, background data including an earlier performance level, user characteristics, and the like.

The apparatus may include dedicated software configured to execute the embodiments described in the present disclosure. The acclimatization application requires RAM-memory 100-400 bytes (×8 bits), preferably 120-180 bytes. Each day requires 4 bytes. Explained by way of example, 150 bytes covers 38 days, wherein the highest VO2max [16 bits], its exercise type [2 bits] and the sum of training load peaks are recorded. Generally, calculation has a window of plurality of days, e.g. 15-100 days, preferably 30-50 days.

Figure 5:
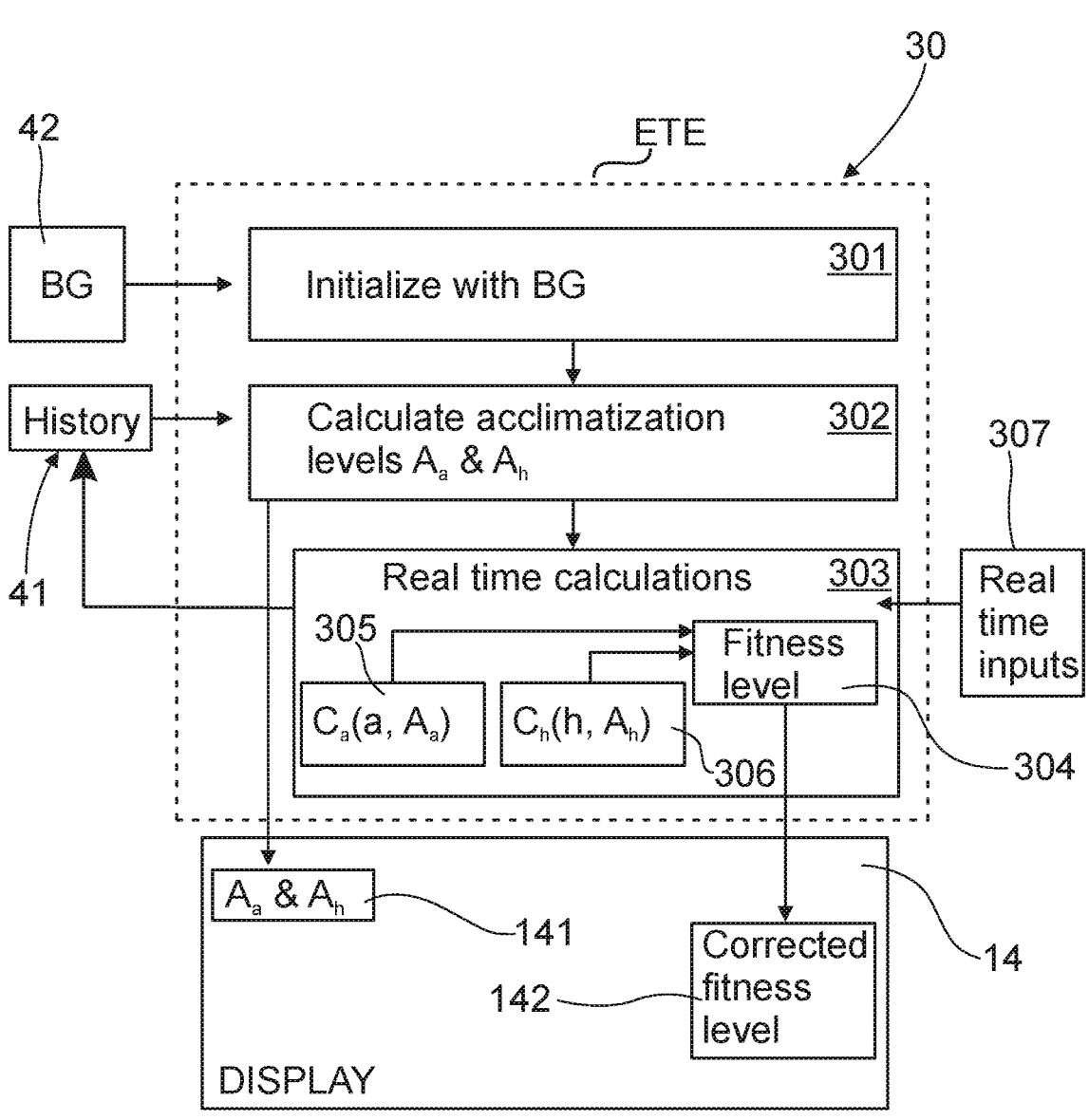
FIG. 5 represents software architecture of calculation process of acclimatization The overall processes are presented in FIG. 1. Training history contains in addition to training data (date, TE) living altitude and/or environmental data (temperature and humidity). In both embodiments (altitude/heat dose) there is initialization, step 10. In the altitude prong the living altitude value is determined for each of the previous 35 days, step 11. Then, the current amount of acclimatization in meters can be calculated, step 12. In the heat dose prong the heat dose sum is calculated in each day in an 18 day window, step 15. Then, the current amount of acclimatization due to heat dose in 0-100% can be calculated, step 16.

FIG. 5 reveals the software architecture. The ETE-library 30 contains plurality of sub functions, a part of which deal with acclimatization calculation. The general initialization using background data (42) starts the procedure, step 301. Background data is in resident memory as well as the history data, which is used, when acclimatization levels due to heat $A_h$ and altitude $A_a$ are calculated, step 302. These levels may be shown in a display.

Real time calculations, step 303 get information from real time inputs 307 (heart rate and external workload, GPS, etc.). History data is updated after each executed exercise, step 41.

There are modules calculating a coefficient for acclimatization due to altitude $C_a(a, A_a)$ 305 and heat dose $C_h(h, A_n)$ 306, respectively. These coefficients are used in the fitness level module calculating the corrected fitness level, step 304. That is finally shown in the display 14. Both corrected fitness level value 142 and acclimatization factors ($A_h$ and $A_a$) 141 are shown to the user.

The invention claimed is:

1. A wearable electronic device operable to be worn by a user, the device comprising:

a heart rate sensor configured to generate heart rate information for the user;

a barometric pressure sensor;

a memory configured to store training history data for the user;

a display; and a processor coupled with the heart rate sensor, the display, the barometric pressure sensor, and the memory, the processor configured to:

determine altitude information for a current day using the barometric pressure sensor, access the training history data for the user, determine a current acclimatization altitude based at least in part on the altitude information of the current day and an acclimatization altitude of a preceding day, calculate an altitude correction factor based at least in part on the current acclimatization altitude and the altitude information of the current day, calculate a corrected VO2max value based at least in part on the altitude correction factor, the acquired training history data, and the heart rate information for the user, and cause the display to present an indication corresponding to the corrected VO2max value.

2. The device of claim 1, wherein the processor is further configured to cause the display to present a training readiness indication; wherein the training readiness indication indicates whether the user is ready to exercise at an altitude corresponding to the determined altitude information for the current day.

3. The device of claim 1, further including a GPS receiver configured to generate position and speed information for the user, wherein the processor is configured to calculate the corrected VO2max value utilizing the generated position and speed information, the altitude correction factor, the heart rate information, and the acquired training history data.

4. The device of claim 1, wherein the processor is further configured to update the training history data stored in the memory utilizing the generated heart rate information and determined altitude information for the current day.

5. The device of claim 1, wherein the training history data indicates altitudes of the wearable electronic device over at least the previous seven days.

6. The device of claim 1, wherein the stored training history data includes VO2max information.

7. A wearable electronic device operable to be worn by a user, the device comprising:

a heart rate sensor configured to generate heart rate information for the user;

a barometric pressure sensor;

a memory configured to store training history data for the user, the training history data including VO2max information and per-day altitudes of the wearable electronic device over at least the previous seven days;

a GPS receiver configured to generate position and speed information for the user;

a display; and a processor coupled with the heart rate sensor, the display, the barometric pressure sensor, the GPS receiver, and the memory, the processor configured to:

determine altitude information of a current day using the barometric pressure sensor, acquire the training history data for the user, determine a current acclimatization altitude based at least in part on the altitude information of the current day and an acclimatization altitude of a preceding day, calculate an altitude correction factor based at least in part on the current acclimatization altitude and the altitude information of the current day, calculate a corrected VO2max value based at least in part on the altitude correction factor, the acquired training history data, the speed information for the user, and the heart rate information for the user, update the training history data stored in the memory utilizing the corrected VO2max value, the current acclimatization altitude, and the determined altitude information of the current day, and cause the display to present the corrected VO2max value and an alert indicating whether the user is ready to exercise at an altitude corresponding to the altitude information of the current day.

* * * * *